US011173107B2

(12) United States Patent
Lin et al.

(10) Patent No.: US 11,173,107 B2
(45) Date of Patent: Nov. 16, 2021

(54) **USES OF *PYRENARIA BUISANENSIS* EXTRACT**

(71) Applicant: TCI Co., Ltd., Taipei (TW)

(72) Inventors: Yung-Hsiang Lin, Taipei (TW); Yu-Ting Lin, Taipei (TW)

(73) Assignee: TCI CO., LTD., Taipei (TW)

( * ) Notice: Subject to any disclaimer, the term of this patent is extended or adjusted under 35 U.S.C. 154(b) by 312 days.

(21) Appl. No.: 16/161,432

(22) Filed: Oct. 16, 2018

(65) Prior Publication Data

US 2019/0117553 A1    Apr. 25, 2019

Related U.S. Application Data

(60) Provisional application No. 62/575,900, filed on Oct. 23, 2017.

(30) Foreign Application Priority Data

Sep. 19, 2018   (TW) .................................. 107132950

(51) Int. Cl.
| | | |
|---|---|---|
| *A61K 8/9789* | (2017.01) | |
| *A61Q 19/00* | (2006.01) | |
| *A61Q 19/02* | (2006.01) | |
| *A61Q 19/08* | (2006.01) | |
| *A61K 36/82* | (2006.01) | |
| *A61P 3/10* | (2006.01) | |
| *A61P 25/28* | (2006.01) | |
| *A61P 9/00* | (2006.01) | |
| *A61K 9/00* | (2006.01) | |

(52) U.S. Cl.
CPC ............ *A61K 8/9789* (2017.08); *A61K 36/82* (2013.01); *A61P 3/10* (2018.01); *A61P 9/00* (2018.01); *A61P 25/28* (2018.01); *A61Q 19/00* (2013.01); *A61Q 19/004* (2013.01); *A61Q 19/007* (2013.01); *A61Q 19/02* (2013.01); *A61Q 19/08* (2013.01); *A61K 9/0014* (2013.01); *A61K 9/0019* (2013.01); *A61K 9/0053* (2013.01); *A61K 2236/33* (2013.01)

(58) Field of Classification Search
CPC .. A61K 2236/33; A61K 36/82; A61K 8/9789; A61K 9/0014; A61K 9/0019; A61K 9/0053; A61P 25/28; A61P 3/10; A61P 9/00; A61Q 19/00; A61Q 19/004; A61Q 19/007; A61Q 19/02; A61Q 19/08
See application file for complete search history.

(56) References Cited

PUBLICATIONS

Global Trees Campaign "Wuwei camellia: *Pyrenaria buisanensis*" <URL: globaltrees.org/threatened-trees/trees/wuwei-camellia/>, retrieved online Sep. 20, 2021, 2020, 3 pages. (Year: 2020).*

Wang, Chen-Lan, et al., "Antioxidant Properties of Extracts from *Camellia tenuifolia*," Taiwan Journal of Forest Science, vol. 21, No. 4: 559565, pp. 559-566 (2006).
Zhan, Yu, et al., "Continuous Countercurrent Extraction and Antioxidant Activity of Flavonoids from *Adinandra nitida* Leaves," Food Science, vol. 31, No. 14, pp. 97-100 (2010).
Hsu, Yen-Chiu, et al., "Anti-oxidative and anti-allergic polyphenols from leaves of *Gordonia axillaris*," (Roxb.) Dietr., 5 pages (2011).
Borkowski, Andrew et al., Toll-Like Receptor 3 Activation Is Required for Normal Skin Barrier Repair Following UV Damage, Journal of Investigative Dermatology, Feb. 2015, vol. 135, No. 2, pp. 569-578.
Chang, Anne Lynn S. et al., "Rejuvenation of Gene Expression Pattern of Aged Human Skin by Broadband Light Treatment: A Pilot Study", Journal of Investigative Dermatology, 2013, vol. 133, pp. 394-402.
Chang, I-Wei et al., "HAS3 Underexpression as an Indicator of Poor Prognosis in Patients with Urothelial Carcinoma of the Upper Urinary Tract and Urinary Bladder", International Society of Oncology and BioMarkers, 2015, 10 pages.
Eckert, Richard L. et al., "Transglutaminase Function in Epidermis", J Invest Dermatol, 2005, vol. 124, pp. 481-492.
Flynn, James M. et al., "SOD2 in Mitochondrial Dysfunction and Neurodegeneration", Free Radic Biol Med, Sep. 2013, vol. 62, pp. 1-21.
Goth, Laszlo, "Catalase Deficiency and Type 2 Diabetes", Diabetes Care, vol. 31, No. 12, Dec. 2008, 1 page.
Iyama, Teruaki et al., "DNA Repair Mechanisms in Dividing and Non-Dividing Cells", DNA Repair (Amst), Aug. 2013, vol. 12, No. 8, pp. 1-42.
Kabashima, Kenji, "New Concept of the Pathogenesis of Atopic Dermatitis: Interplay Among the Barrier, Allergy, and Pruritus as a Trinity", Journal of Dermatological Science, 2013, vol. 70, pp. 3-11.
Kumar, Vinod et al., "A Keratin Scaffold Regulates Epidermal Barrier Formation, Mitochondrial Lipid Composition, and Activity", The Journal of Cell Biology, 2015, vol. 211, No. 5, pp. 1057-1075.
Lieber, Michael R., "The Mechanism of Double-Strand DNA Break Repair by the Nonhomologous DNA End Joining Pathway", Annu Rev Biochem, 2010, vol. 79, pp. 181-211.
Liu, Ganqiang et al., "Specifically Neuropathic Gaucher's Mutations Accelerate Cognitive Decline in Parkinson's", Annals of Neurology, Nov. 2016, vol. 80, No. 5, pp. 674-685.
McGrath, John A. et al., "The Filaggrin Story: Novel Insights Into Skin-Barrier Function and Disease", Trends in Molecular Medicine, 2007, vol. 14, No. 1, pp. 20-27.

(Continued)

*Primary Examiner* — Aaron J Kosar
(74) *Attorney, Agent, or Firm* — Christensen, Fonder, Dardi & Herbert PLLC

(57) ABSTRACT

A method for at least one of whitening skin, improving skin condition, protecting skin, and treating skin disease is provided, wherein the method comprises administering to a subject in need an effective amount of a *Pyrenaria buisanensis* extract. A method for at least one of preventing cardiovascular disease, treating cardiovascular disease, preventing diabetes, treating diabetes, preventing neurodegenerative disease, and treating neurodegenerative disease is also provided, wherein the method comprises administering to a subject in need an effective amount of a *Pyrenaria buisanensis* extract.

15 Claims, 7 Drawing Sheets

(56) References Cited

PUBLICATIONS

McLean, WH Irwin et al., "Disorders of Keratinisation: From Rare to Common Genetic Diseases of Skin and Other Opithelial Tissues", The Ulster Medical Journal, Jan. 2007, vol. 76, No. 2, pp. 72-82.
Pereda, Maria Del Carmen Velazquez et al., "Expression of Differential Genes Involved in the Maintenance of Water Balance in Human Skin by Piptadenia Colubrina Extract", Journal of Cosmetic Dermatology, 2010, vol. 9, pp. 35-43.
Russell, Laura J. et al., "Mutations in the Gene for Transglutaminase 1 in Autosomal Recessive Lamellar Ichthyosis", Nature Genetics, Mar. 1995, vol. 9, pp. 279-283.
Sandilands, Aileen et al., "Filaggrin in the Frontline: Role in Skin Barrier Function and Disease", Journal of Cell Science, 2009, vol. 122, No. 9, pp. 1285-1294.
Sayo, Tetsuya et al., "Hyaluronan Synthase 3 Regulates Hyaluronan Synthesis in Cultured Human Keratinocytes", The Journal of Investigative Dermatology, vol. 118, No. 1, Jan. 2002, pp. 43-48.
Schuch, Andre Passaglia et al., "Sunlight Damage to Cellular DNA: Focus on Oxidatively Generated Lesions", Free Radical Biology and Medicine, 2017, vol. 107, pp. 110-124.
Sinha, Santosh, "Anti-Oxidant Gene Expression Imbalance, Aging and Down Syndrome", Life Sciences, 2005, vol. 76, pp. 1407-1426.
Weyemi, Urbain et al., SOD2 Deficiency Promotes Aging Phenotypes in Mouse Ski, Aging, Feb. 2012, vol. 4, No. 2, pp. 116-118.
Yang, Jun-Mo et al., "Novel Mutations of the Transglutaminase 1 Gene in Lamellar Ichthyosis", The Journal of Investigative Dermatology, Aug. 2001, vol. 117, No. 8, pp. 214-218.
Yi, Cho, "Survey of Endemic Medicinal Seed Plant Resources in Taiwan," *Chinese Doctoral Dissertations Full-text Database Agriculture Science and Technology*, 2012, No. 1 (131 pages).

\* cited by examiner

USES OF *PYRENARIA BUISANENSIS* EXTRACT

CROSS REFERENCE TO RELATED APPLICATIONS

This application claims priority to U.S. Provisional Application Ser. No. 62/575,900 filed on Oct. 23, 2017, and to Taiwan Patent Application No. 107132950 filed on Sep. 19, 2018, the disclosures of which are incorporated herein in their entirety by reference.

FIELD OF THE INVENTION

The present invention relates to the use of a *Pyrenaria buisanensis* extract, including the use of *Pyrenaria buisanensis* extract in whitening skin, improving skin condition, protecting skin, and/or treating skin disease. The present invention also relates to the use of *Pyrenaria buisanensis* extract in preventing cardiovascular disease, treating cardiovascular disease, preventing diabetes, treating diabetes, preventing neurodegenerative disease, and/or treating neurodegenerative disease.

BACKGROUND OF THE INVENTION

Skin, which is the first defense line protecting the body against harmful factors from the external environment, plays an important role in water retention, warm retention and sensation. The increase in age as well as the factors such as ultraviolet (UV) rays, radiation, and environmental pollution all may reduce the water content of skin and cause the losses of collagen and elastin, thereby causing the occurrence of skin aging phenomena such as wrinkles, skin sagging, skin dullness and roughness, and may even destroy the DNA of skin cells that may accelerate the death of skin cells or lead to skin lesions, and thus, result in skin cancer.

Nowadays, people pay much more attention on the issues of skin whitening, skin moisture and anti-aging, hence there are much more approaches and diverse beauty products in the market, such as orally administering collagen, percutaneously administering hyaluronic acid, and injecting *botulinus*. However, the molecular structures of collagen and hyaluronic acid are too large to be effectively absorbed into human body via oral or percutaneous administration, and thus the effect of the supplement of collagen and/or hyaluronic acid is limited. Although the injection with *botulinus* can reduce skin fine lines, the effect is temporary and thus a regular injection is required. Furthermore, the injection with *botulinum* is costly and may cause the side effects such as edema or blood stasis around the injection site, eyelid or eyebrow sagging, headache, allergy, facial asymmetry, and unnatural facial expression.

It was revealed by researches that increasing the expression level of the genes such as SOD2, CAT, MSH2, Tgm1, Keratin14, FLG, GBA and/or HAS3 is beneficial to enhancing the antioxidant capability of cells, repairing damaged DNA and proteins in cells, maintaining cell structure, increasing the synthesis of hyaluronic acid, and/or increasing the water content of skin. Inventors of the present invention investigated by using natural materials and found that *Pyrenaria buisanensis* extract can increase the expressions of SOD2, CAT, MSH2, Tgm1, Keratin14, FLG, GBA and HAS3 genes, enhance the antioxidant capability of skin, reduce melanin of skin, reduce skin sagging, and increase the water content of skin, and thus, can be used for moisturizing skin, whitening skin, tightening skin, reducing skin fine lines, anti-skin aging, alleviating dry skin, promoting the production of hyaluronic acid, assisting in maintenance of skin health, anti-photodamage, and/or repairing skin tissues, and also can be used for preventing, treating or regulating diseases or physiological functions related to the aforementioned genes.

SUMMARY OF THE INVENTION

An objective of the present invention is to provide a use of a *Pyrenaria buisanensis* extract in at least one of moisturizing skin, whitening skin, tightening skin, reducing skin fine lines, anti-skin aging, alleviating dry skin, promoting the production of hyaluronic acid, and assisting in maintenance of skin health. Preferably, the extract is provided by extracting *Pyrenaria buisanensis* with a polar solvent, and the polar solvent is selected from a group consisting of water, C1-C4 alcohols, and combinations thereof. Preferably, the extract is an extract of leaves of *Pyrenaria buisanensis*. Preferably, the extract is taken through transdermal or oral route.

Another objective of the present invention is to provide a use of the aforesaid *Pyrenaria buisanensis* extract in the manufacture of a pharmaceutical composition, wherein the pharmaceutical composition is for at least one of anti-photodamage, repairing skin tissues, preventing skin disease, and treating skin disease. Preferably, the skin disease is a disease related to dry skin. Preferably, the pharmaceutical composition is provided in a form for transdermal administration, oral administration, or subcutaneous administration.

Still another objective of the present invention is to provide a use of the aforesaid *Pyrenaria buisanensis* extract in the manufacture of a pharmaceutical composition, wherein the pharmaceutical composition is for at least one of preventing cardiovascular disease, treating cardiovascular disease, preventing diabetes, treating diabetes, preventing neurodegenerative disease, and treating neurodegenerative disease. Preferably, the cardiovascular disease is stroke, and the neurodegenerative disease is Alzheimer's disease. Preferably, the pharmaceutical composition is provided in a form for transdermal administration, oral administration, or subcutaneous administration.

Yet another objective of the present invention is to provide a use of the aforesaid *Pyrenaria buisanensis* extract in the manufacture of a pharmaceutical composition, wherein the pharmaceutical composition is for increasing the expressions of at least one of SOD2 gene, CAT gene, MSH2 gene, Tgm1 gene, Keratin14 gene, FLG gene, GBA gene and HAS3 gene. Preferably, the pharmaceutical composition is provided in a form for transdermal administration, oral administration, or subcutaneous administration.

Yet another objective of the present invention is to provide a composition for whitening skin, improving skin condition, and/or protecting skin. The composition comprises an effective amount of the aforesaid *Pyrenaria buisanensis* extract. Preferably, the composition is for moisturizing skin, tightening skin, reducing skin fine lines, and/or alleviating dry skin. Preferably, the composition is for anti-skin aging, assisting in maintenance of skin health, anti-photodamage, repairing skin tissues, and/or preventing skin disease. Preferably, the composition is a skin care product composition or a food product composition, and the skin care product composition provided in a form for transdermal administration or oral administration.

Yet another objective of the present invention is to provide a pharmaceutical composition for treating skin disease, preventing cardiovascular disease, treating cardiovascular disease, preventing diabetes, treating diabetes, preventing neurodegenerative disease, and/or treating neurodegenerative disease. The pharmaceutical composition comprises an effective amount of the aforesaid *Pyrenaria buisanensis* extract. Preferably, the skin disease is a disease related to dry skin, the cardiovascular disease is stroke, and the neurodegenerative disease is Alzheimer's disease. Preferably, the pharmaceutical composition is provided in a form for transdermal administration, oral administration, or subcutaneous administration.

Yet another objective of the present invention is to provide a pharmaceutical composition for increasing the expressions of SOD2 gene, CAT gene, MSH2 gene, Tgm1 gene, Keratin14 gene, FLG gene, GBA gene and/or HAS3 gene. The pharmaceutical composition comprises an effective amount of the aforesaid *Pyrenaria buisanensis* extract. Preferably, the pharmaceutical composition is provided in a form for transdermal administration, oral administration, or subcutaneous administration.

Yet another objective of the present invention is to provide a method for at least one of whitening skin, improving skin condition, protecting skin, and treating skin disease, comprising administering to a subject in need an effective amount of the aforesaid *Pyrenaria buisanensis* extract. In the method of the present invention, the *Pyrenaria buisanensis* extract can be administered to the subject as the skin care product composition, the food composition, or the pharmaceutical composition described above. Preferably, the method is for moisturizing skin, tightening skin, reducing skin fine lines, and/or alleviating dry skin. Preferably, the method is for anti-skin aging, assisting in maintenance of skin health, anti-photodamage, repairing skin tissues, and/or preventing skin disease. Preferably, the skin disease is a disease related to dry skin.

Yet another objective of the present invention is to provide a method for at least one of preventing cardiovascular disease, treating cardiovascular disease, preventing diabetes, treating diabetes, preventing neurodegenerative disease, and treating neurodegenerative disease, comprising administering to a subject in need an effective amount of the aforesaid *Pyrenaria buisanensis* extract. In the method of the present invention, the *Pyrenaria buisanensis* extract can be administered to the subject as the pharmaceutical composition described above. Preferably, the cardiovascular disease is stroke, and the neurodegenerative disease is Alzheimer's disease.

Yet another objective of the present invention is to provide a method for increasing the expressions of SOD2 gene, CAT gene, MSH2 gene, Tgm1 gene, Keratin14 gene, FLG gene, GBA gene and/or HAS3 gene, comprising administering to a subject in need an effective amount of the aforesaid *Pyrenaria buisanensis* extract. In the method of the present invention, the *Pyrenaria buisanensis* extract can be administered to the subject as the pharmaceutical composition described above.

The detailed technology and preferred embodiments implemented for the present invention are described in the following paragraphs accompanying the appended drawings for people skilled in this field to well appreciate the features of the claimed invention.

BRIEF DESCRIPTION OF THE DRAWINGS

FIG. 3, FIG. 4 and FIG. 5 show the effects of the *Pyrenaria buisanensis* extract of the present invention on increasing the expressions of SOD2, CAT and MSH2 genes, wherein FIG. 3 shows the expression level of SOD2 gene of cells in each group, FIG. 4 shows the expression level of CAT gene of cells in each group, and FIG. 5 shows the expression level of MSH2 gene of cells in each group, and wherein, the cells in the control group were cultivated in a medium free of *Pyrenaria buisanensis* extract for 6 hours, those in the "UVA group" were cultivated in a medium free of *Pyrenaria buisanensis* extract for 6 hours, and then irradiated with UVA for 6 hours, those in the "Extract (1)—6 hr group" and "Extract (1)—24 hr group" were independently cultivated in a medium that was externally added with *Pyrenaria buisanensis* extract (to the final concentration of 1 mg/mL) for 6 hours and 24 hours respectively, and then irradiated with UVA for 6 hours, and those in the "Extract (2)—6 hr group" and "Extract (2)—24 hr group" were independently cultivated in a medium that was externally added with *Pyrenaria buisanensis* extract (to the final concentration of 2 mg/mL) for 6 hours and 24 hours respectively, and then irradiated with UVA for 6 hours;

FIG. 6, FIG. 7 and FIG. 8 show the effects of the *Pyrenaria buisanensis* extract of the present invention on increasing the expressions of Tgm1, Keratin14, FLG, GBA and HAS3 genes, wherein FIG. 6 shows the expression levels of Tgm1 gene and Keratin14 gene of cells in each group, FIG. 7 shows the expression level of FLG gene of cells in each group, and FIG. 8 shows the expression levels of GBA gene and HAS3 gene of cells in each group, and wherein, the cells in the control group were cultivated in a medium free of *Pyrenaria buisanensis* extract for 6 hours, those in the "Extract group" were cultivated in a medium that was externally added with *Pyrenaria buisanensis* extract for 6 hours.

DESCRIPTION OF THE PREFERRED EMBODIMENTS

Figure 1:
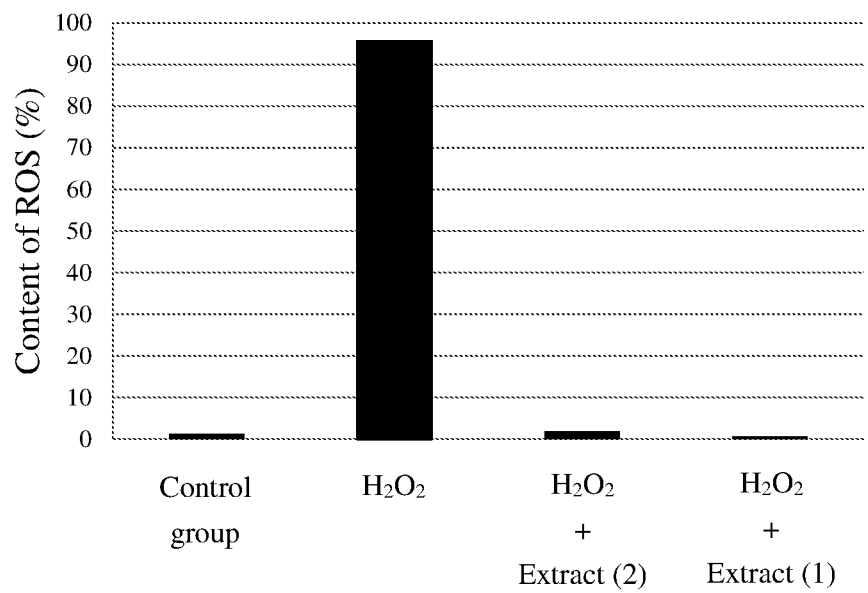
FIG. 1 shows the effect of the *Pyrenaria buisanensis* extract of the present invention on reducing ROS content in cells, wherein the cells in the control group were cultivated in a medium free of *Pyrenaria buisanensis* extract for 1 hour, those in the "$H_2O_2$ group" were cultivated in a medium free of *Pyrenaria buisanensis* extract for 1 hour, and then treated with $H_2O_2$ for 1 hour, and those in the "$H_2O_2$+extract (1) group" and "$H_2O_2$+extract (2) group" were independently cultivated in a medium that was externally added with *Pyrenaria buisanensis* extract (to the final concentration of 1 mg/mL and 2 mg/mL, respectively) for 1 hour, and then treated with $H_2O_2$ for 1 hour.

The following will describe some of the embodiments of the present invention in detail. However, without departing from the spirit of the present invention, the present invention may be embodied in various embodiments and should not be limited to the embodiments described in the specification. In addition, unless otherwise indicated herein, the expressions "a," "an," "the," or the like recited in the specification of the present invention (especially in the claims) are intended to include both the singular and plural forms. The term "treat" or "treating" recited in this specification should not be construed as treating a subject until the subject completely recovered, but should include maintaining the progression or symptoms of the diseases in a substantially static state, increasing the recovery rate of a subject, alleviating the severity of a particular condition of illness, or increasing the life quality of patients. The term "prevent" or "preventing" recited in this specification refers to inhibiting or avoiding a particular condition of illness from breaking out, maintaining good health in a sensitive subject, or establishing the ability of a sensitive subject to tolerate diseases. The term "regulate" or "regulating" recited in this specification refers to upregulating (includes inducing, stimulating, and enhancing) or downregulating (includes inhibiting and weakening) the physiological functions in a subject toward a normal state. The term "subject" recited in this specification refers to a mammalian, including human and non-human animals.

It was revealed by researches that an increment in the expression levels of SOD2 gene (superoxidase dismutase producing gene) and CAT gene (catalase producing gene) is beneficial to enhancement of the antioxidant capability of cells. It has also been known that the low expression or deletion of SOD2 gene and/or CAT gene is related to skin aging and the occurrences of cardiovascular diseases, diabetes, and Alzheimer's disease, and these can be noted in "Anti-oxidant gene expression imbalance, aging and Down syndrome. *Life Sciences.* 76: 1407-1426 (2005)," "Catalase Deficiency and Type 2 Diabetes. *Diabetes Care.* 31(12): e93 (2008)," "SOD2 deficiency promotes aging phenotypes in mouse skin. AGING. 4(2): 116-118 (2012)," "SOD2 in Mitochondrial Dysfunction and Neurodegeneration. *Free Radic Biol Med.* 62: 4-12 (2013)," and "Sunlight damage to cellular DNA: Focus on oxidatively generated lesions. *Free Radical Biology and Medicine.* 107: 110-124 (2017)," which are entirely incorporated hereinto by reference. Therefore, if the expression of SOD2 and/or CAT gene can be increased effectively, the following effects could be provided: anti-skin aging (e.g., anti-skin photoaging), preventing cardiovascular disease, treating cardiovascular disease, preventing diabetes, treating diabetes, preventing Alzheimer's disease, and treating Alzheimer's disease.

Researches have also revealed that an increment in the expression level of MSH2 gene of cells is beneficial to the repair of damaged DNA and proteins, and these can be noted in "DNA repair mechanisms in dividing and non-dividing cells. *DNA repair (Amst).* 12(8): 620-636 (2013)" and "Repairing Double-Strand DNA Breaks. *Nature Education.* 3(9): 26 (2010)," which are entirely incorporated hereinto by reference. It has also been known that the low expression or deletion of MSH2 gene is related to skin aging, and these can be noted in "Rejuvenation of Gene Expression Pattern of Aged Human Skin by Broadband Light Treatment: A Pilot Study. *Journal of Investigative Dermatology.* 133: 394-402 (2013)", which is entirely incorporated hereinto by reference. Therefore, if the expression of MSH2 gene can be increased effectively, the effect of anti-skin aging can be provided.

An increment in the expression levels of Tgm1 and Keratin14 genes is beneficial to maintenance of cell structure, and these can be noted in "A keratin scaffold regulates epidermal barrier formation, mitochondrial lipid composition, and activity. *J. Cell Biol.* 211(5): 1057-1075 (2015)" and "Transglutaminase Function in Epidermis. *J Invest Dermatol.* 124(3): 481-492 (2005)," which are entirely incorporated hereinto by reference. It has been known that the low expression or deletion of Tgm1 and/or Keratin14 gene is related to skin aging and the occurrence of a disease related to dry skin, and these can be noted in "Mutations in the gene for transglutaminase 1 in autosomal recessive lamellar ichthyosis. *Nat Genet.* 9(3): 279-283 (1995)," "Transglutaminase Function in Epidermis. *J Invest Dermatol.* 124(3): 481-492 (2005)," "Novel Mutations of the Transglutaminase 1 Gene in Lamellar Ichthyosis. *J Invest Dermatol.* 117(8): 214-218 (2001)," and "Disorders of keratinisation: from rare to common genetic diseases of skin and other epithelial tissues. *Ulster Med J.* 76 (2): 72-82 (2007)," which are entirely incorporated hereinto by reference. Therefore, if the expression of Tgm1 and/or Keratin14 gene can be increased effectively, the following effects could be provided: assisting in maintenance of skin health, moisturizing skin, tightening skin, reducing skin fine lines, alleviating dry skin, anti-skin aging, preventing a disease related to dry skin, and treating a disease related to dry skin.

An increment in the expression levels of the GBA, FLG and HAS3 genes is beneficial to the formation of skin barrier, increase in hyaluronic acid synthesis, and increase in the water content of cells, and these can be noted in "Hyaluronan Synthase 3 Regulates Hyaluronan Synthesis in Cultured Human Keratinocytes. *The Journal of Investigative Dermatology.* 118: 43-48 (2002)," "Toll-like receptor 3 activation is required for normal skin barrier repair following UV damage. *J Invest Dermatol.* 135(2): 569-578 (2015)," "Expression of differential genes involved in the maintenance of water balance in human skin by *Piptadenia colubrina* extract. *J Cosmet Dermatol.* 9(1): 35-43 (2010)," "New concept of the pathogenesis of atopic dermatitis: Interplay among the barrier, allergy, and pruritus as a trinity. *J Dermatol Sci.* 70(1): 3-11 (2013)," and "Filaggrin in the frontline: role in skin barrier function and disease. *Journal of Cell Science.* 122(9): 1285-1294 (2009)," which are entirely incorporated hereinto by reference. It has been known that the low expression or deletion of GBA, FLG and/or HAS3 gene is related to skin aging and dry skin, and these can be noted in "HAS3 underexpression as an indicator of poor prognosis in patients with urothelial carcinoma of the upper urinary tract and urinary bladder. *Tumor Biol.* 36(7): 5441-5450 (2015)," "Specifically Neuropathic Gaucher's Mutations Accelerate Cognitive Decline in Parkinson's. *Ann Neurol.* 80(5): 674-685 (2016)," "Filaggrin in the frontline: role in skin barrier function and disease. *Journal of Cell Science.* 122(9): 1285-1294 (2009)," and "The filaggrin story: novel insights into skin-barrier function and disease. *Trends Mol Med.* 14(1): 20-27 (2008)," which are entirely incorporated hereinto by reference. Therefore, if the expression of GBA, FLG and/or HAS3 gene can be increased effectively, the following effects could be provided: assisting in maintenance of skin health, moisturizing skin, tightening skin, reducing skin fine lines, anti-skin aging, and/or alleviating dry skin.

*Pyrenaria buisanensis*, a plant of unique species in Taiwan, which belonging to the family Theaceae and genus *Pyrenaria*. Inventors of the present invention discovered that *Pyrenaria buisanensis* extract can effectively increase the expressions of SOD2, CAT, MSH2, Tgm1, Keratin14, FLG, GBA, and HAS3 genes. Therefore, the present invention relates to the use of *Pyrenaria buisanensis* extract, including: using *Pyrenaria buisanensis* extract in moisturizing skin, whitening skin, tightening skin, reducing skin fine lines, anti-skin aging, alleviating dry skin, and/or assisting in maintenance of skin health, using *Pyrenaria buisanensis* extract in manufacturing a pharmaceutical composition, providing a skin care product composition, a food product composition, or a pharmaceutical composition comprising an effective amount of a *Pyrenaria buisanensis* extract, and providing a method of administering to a subject in need an effective amount of the aforesaid skin care product composition, food product composition, or pharmaceutical composition. The skin care product composition provided in accordance with the present invention is for moisturizing skin, whitening skin, tightening skin, reducing skin fine lines, anti-skin aging, and/or alleviating dry skin. The food product composition provided in accordance with the present invention is for assisting in maintenance of skin health. The pharmaceutical composition provided in accordance with the present invention is for anti-photodamage, repairing skin tissues, preventing skin disease, and/or treating skin disease. The pharmaceutical composition provided in accordance with the present invention is also for at least one of preventing cardiovascular disease, treating cardiovascular disease, preventing diabetes, treating diabetes, preventing neurodegenerative disease, and treating neurodegenerative disease. For example, the pharmaceutical composition is for preventing a disease related to dry skin (e.g., ichthyosis), treating a disease related to dry skin, preventing stroke, treating stroke, preventing Alzheimer's disease, and/or treating Alzheimer's disease. In addition, the pharmaceutical composition and the method provided in accordance with the present invention are also for increasing the expressions of SOD2, CAT, MSH2, Tgm1, Keratin14, FLG, GBA, and/or HAS3 genes.

The *Pyrenaria buisanensis* extract adopted in accordance with the present invention could be provided by extracting the leaves of *Pyrenaria buisanensis* with a polar solvent, wherein the polar solvent can be a water, C1-C4 alcohols, or a combination thereof. There is no particular limitation of the part of the *Pyrenaria buisanensis* material from which the *Pyrenaria buisanensis* extract is produced. And, the *Pyrenaria buisanensis* extract adopted in accordance with the present invention could be provided by extracting the whole plant of *Pyrenaria buisanensis* or the roots, stems, leaves, and/or flowers of *Pyrenaria buisanensis*. In some embodiments of the present invention, the leaves of *Pyrenaria buisanensis* were used to prepare a *Pyrenaria buisanensis* extract. Furthermore, the amount of the solvent used in the extraction step is not critical and is generally capable of evenly dispersing the materials to be extracted. For example, in the extraction step, the extraction solvent and the leaves of *Pyrenaria buisanensis* could be used at a weight ratio ranging from 1:1 to 20:1 (extraction solvent: leaves of *Pyrenaria buisanensis*). In one embodiment of the present invention, the extraction was carried out with the use of extraction solvent and leaves of *Pyrenaria buisanensis* at a weight ratio of 10:1 (extraction solvent: leaves of *Pyrenaria buisanensis*).

In extraction step, the extraction could be conducted for a suitable period of time depending on the extraction solvent that is adopted. For example, when the extraction solvent is water and the weight ratio of water and the leaves of *Pyrenaria buisanensis* ranges from about 1:1 to 20:1 (water: leaves of *Pyrenaria buisanensis*), the extraction is usually conducted for 0.5 to 2 hours. Furthermore, prior to or when conducting the extraction step, one or more other operations such as heating, cooling, stirring, and ultrasonication could be optionally performed, or the *Pyrenaria buisanensis* material could be crushed prior to conducting the extraction step, to further enhance the extraction efficiency. For example, the extraction could be conducted at 75° C. to 95° C. In one embodiment of the present invention, the extraction was conducted at 85° C. for 0.5 hours.

The *Pyrenaria buisanensis* extract adopted in accordance with the present invention could be a stock liquid extract directly obtained from the extraction, and also could be a product obtained by carrying out one or more optional steps such as filtration, sterilization, concentration, and dilution on the stock liquid extract to facilitate the use of the liquid extract. To achieve an extraction efficiency as high as possible, the *Pyrenaria buisanensis* material could optionally be repeatedly extracted with the same or different extraction solvents, and the liquid extracts thus obtained are combined to provide the liquid extract. For example, the liquid extract could be subjected to the vacuum concentration to maintain the stability of the active ingredients in the *Pyrenaria buisanensis* extract during conservation. Also, the temperature of the vacuum concentration could be optionally adjusted. For example, the vacuum concentration could be conducted at 45° C. to 70° C. In one embodiment of the present invention, the vacuum concentration was conducted at 55° C. to 65° C.

Depending on the desired purpose(s), the skin care product composition provided in accordance with the present invention could be administered to a subject in need systemically or topically, and could be provided in any suitable form without particular limitations. For example, the skin care product composition could be provided in the form of an emulsion, a cream, a gel (e.g., a hydrogel), or a solution (e.g., an essence, a lotion) for external use, but is not limited thereby.

The food product composition of the present invention could be provided in any suitable form without particular limitations. For example, the food product composition could be manufactured in the form suitable for eating or drinking, such as in the form of a health food and a beauty beverage, but is not limited thereby.

The pharmaceutical composition provided in accordance with the present invention could be administered to a subject in need systemically or topically, and could be delivered by various drug delivery systems (DDSs), such as oral drug delivery system, transdermal drug delivery system, injection delivery system, etc. For example, to enhance bioavailability, control drug release speed, target the lesion precisely and reduce side effects, the pharmaceutical composition could be delivered by a liposome, a microcapsule, nanoparticles, microneedles, but is not limited thereby.

Depending on the desired purpose(s), the pharmaceutical composition of the present invention could be provided in any suitable form without particular limitations. For example, the pharmaceutical composition could be administered to a subject in need by an oral or parenteral (such as transdermal administration or subcutaneous injection) route, but is not limited thereby. Depending on the form and purpose(s), a suitable carrier could be chosen and used to provide the pharmaceutical composition. Examples of the carrier include excipients, diluents, auxiliaries, stabilizers, absorption retarders, disintegrating agent, hydrotropic agents, emulsifiers, antioxidants, adhesives, binders, tackifiers, dispersants, suspending agents, lubricants, hygroscopic agents, etc.

As a form for oral administration, the pharmaceutical composition could comprise any pharmaceutically acceptable carrier that will not adversely affect the desired effects of the active ingredient (i.e., *Pyrenaria buisanensis* extract). Examples of the suitable carrier include, but are not limited to, water, saline, dextrose, glycerol, ethanol or its analogs, oil (e.g., olive oil, castor oil, cottonseed oil, peanut oil, corn oil, germ oil), polyethylene glycol, starch, kaolinite, bentonite, sodium citrate, gelatin, agar, carboxymethyl cellulose, gum arabic, alginic acid and its salts, glyceryl monostearate, calcium stearate, and combinations thereof. The pharmaceutical composition could be provided by any suitable method in any suitable form for oral administration, such as in the form of a tablet (e.g., sugar-coated tablet), a pill, a capsule, granules, a pulvis, a fluidextract, a solution, syrup, a suspension, a tincture, but is not limited thereby.

As a form for transdermal administration, the pharmaceutical composition provided in accordance with the present invention could also comprise any pharmaceutically acceptable carrier that will not adversely affect the desired effects of the active ingredient (i.e., *Pyrenaria buisanensis* extract). Examples of the suitable carrier include, but are not limited to, water, mineral oil, propylene glycol, polyethylene oxide, liquid petrolatum, sorbitan monostearate, polysorbate 60. The pharmaceutical composition could be provided by any suitable method in any suitable form for transdermal administration, such as in the form of a patch, an emulsion, a cream, a gel (e.g., a hydrogel), a paste (e.g., a dispersing paste, an ointment), a spray, a solution (e.g., a suspension) for external use, but is not limited thereby.

As for the form of injections or drips suitable for subcutaneous administration, the pharmaceutical composition could comprise one or more ingredient(s), such as an isotonic solution, a salt-buffered saline (e.g., phosphate-buffered saline or citrate-buffered saline), a hydrotropic agent, an emulsifier, a 5% sugar solution, and other carriers. Alternatively, the pharmaceutical composition could be prepared as a pre-injection solid. The pre-injection solid could be provided in a form which is soluble in other solutions or suspensions, or in an emulsifiable form. A desired injection is provided by dissolving the pre-injection solid in other solutions or suspensions or emulsifying it prior to being administered to a subject in need.

Optionally, the skin care product composition, the food product composition, and the pharmaceutical composition provided in accordance with the present invention could further comprise a suitable amount of additives, such as a flavoring agent, a toner, or a coloring agent for enhancing the palatability and the visual perception of the food product composition or the pharmaceutical composition, and/or a buffer, a conservative, a preservative, an antibacterial agent, or an antifungal agent for improving the stability and storability of the skin care product composition, the food product composition, or the pharmaceutical composition. In addition, the skin care product composition and the pharmaceutical composition could optionally further comprise one or more other active ingredient(s), or to be used in combination with a medicament comprising one or more other active ingredient(s), to further enhance the effect of the skin care product composition and the pharmaceutical composition, or to increase the application flexibility and adaptability of the preparation thus provided, as long as the other active ingredients do not adversely affect the desired effects of the active ingredient of the present invention (i.e., *Pyrenaria buisanensis* extract).

Depending on the needs, age, body weight and health conditions of the subject as well as the purpose(s), the skin care product composition, the food product composition, and the pharmaceutical composition provided in accordance with the present invention could be administered at various administration frequencies, such as once a day, multiple times a day, once every few days, etc. In addition, the concentration of the *Pyrenaria buisanensis* extract in the skin care product composition, the food product composition, and the pharmaceutical composition could be adjusted depending on the requirements of practical application.

In the use of *Pyrenaria buisanensis* extract in moisturizing skin, whitening skin, tightening skin, reducing skin fine lines, anti-skin aging, alleviating dry skin, and/or assisting in maintenance of skin health provided in accordance with the present invention, the *Pyrenaria buisanensis* extract could be provided as a skin care product composition or a food product composition. The administration type, administration route, administration form, administration frequency and uses of the skin care product composition and the food product composition are all in line with the above descriptions.

As described above, the present invention also provides a method for at least one of whitening skin, improving skin condition, protecting skin, and treating skin disease, comprising administering to a subject in need an effective amount of a *Pyrenaria buisanensis* extract, wherein the term "a subject in need" refers to a subject having a requirement for improving skin condition and/or preventing the skin condition from getting worse, a subject having skin lesion phenomena, a subject suffering from skin disease, and/or a subject with high-risk of getting skin disease. For example, the subject is one having thickening of skin keratin, generation of skin wrinkles, generation of skin dark spots, skin dullness, desiccation and desquamation of skin, skin sagging, and/or skin aging, one working outdoors for a long time, one suffering from a disease related to dry skin, and/or one with high-risk of a disease related to dry skin, but is not limited thereby. In the method, the *Pyrenaria buisanensis* extract could be administered to the subject as the skin care product composition, the food product composition, or the pharmaceutical composition described above. The administration type, administration route, administration form, administration frequency and uses of the skin care product composition, the food product composition, and the pharmaceutical composition are also all in line with the above descriptions.

The present invention also provides a method for at least one of preventing cardiovascular disease, treating cardiovascular disease, preventing diabetes, treating diabetes, preventing neurodegenerative disease, and treating neurodegenerative disease, comprising administering to a subject in need an effective amount of a *Pyrenaria buisanensis* extract, wherein the term "a subject in need" refers to a subject suffering from cardiovascular disease, suffering from diabetes, suffering from neurodegenerative disease, with high risk of cardiovascular disease, with high risk of diabetes, and/or with high risk of neurodegenerative disease. In the method, the *Pyrenaria buisanensis* extract could be administered to the subject as the pharmaceutical composition described above. The administration type, administration route, administration form, administration frequency and uses of the pharmaceutical composition are also all in line with the above descriptions.

The present invention also provides a method for increasing the expressions of SOD2 gene, CAT gene, MSH2 gene, Tgm1 gene, Keratin14 gene, FLG gene, GBA gene and/or HAS3 gene, comprising administering to a subject in need an effective amount of a *Pyrenaria buisanensis* extract, wherein the term "a subject in need" refers to a subject whose SOD2 gene, CAT gene, MSH2 gene, Tgm1 gene, Keratin14 gene, FLG gene, GBA gene and/or HAS3 gene is deleted, mutated, or low-expressed. In the method, the *Pyrenaria buisanensis* extract could be administered to the subject in need as the pharmaceutical composition described above. The administration type, administration route, administration form, administration frequency and uses of the composition are all in line with the above descriptions.

The present invention will be further illustrated in detail with specific examples as follows. However, the following examples are provided only for illustrating the present invention and the scope of the present invention is not limited thereby. The scope of the present invention will be indicated in the appended claims.

EXAMPLES

Preparation Examples

Preparation of *Pyrenaria buisanensis* Extract

The *Pyrenaria buisanensis* plants were provided by Dr. Cecilia Koo Botanic Conservation Center (KBCC; Taiwan) and subjected to the following steps to provide a *Pyrenaria buisanensis* extract:
I. Washing leaves of *Pyrenaria buisanensis* with reverse osmosis (RO) water, optionally, the aforesaid washing step could be repeated;
II. Mixing the washed leaves of *Pyrenaria buisanensis* with water (the weight ratio of leaves of *Pyrenaria buisanensis* and water=1:10) to provide a mixture, and then subjecting the mixture to an extraction at 85° C. for 0.5 hours to provide a liquid extract;
III. Cooling the liquid extract to the room temperature, and then filtrating the same with a 400-mesh filter to provide a filtrate; and
IV. Concentrating the filtrate under vacuum at 55° C. to 65° C. to provide a concentrated liquid extract (i.e., *Pyrenaria buisanensis* extract of the present invention).

Example 1

Effects of *Pyrenaria buisanensis* Extract on Enhancing the Antioxidant Capability of Skin It has been known that an excessive content of reactive oxygen species (ROS) in skin cells may cause the destruction of cellular tissues and DNA damage, and thus, result in skin aging. To avoid the toxicity of ROS to skin cells, organism will secrete the enzyme such as superoxide dismutase (SOD) to decompose the excessive ROS in the body. To confirm the effects of *Pyrenaria buisanensis* extract of the present invention on inhibiting the production of ROS in skin cells and enhancing the activity of SOD in skin cells, the following experiments were conducted.

(1-1) Examination of the Content of ROS

Human skin fibroblasts (CCD-966SK; purchased from ATCC) were cultivated in a MEM medium (Minimum essential medium; purchased from Gibco company, product number: 61100-061) for 24 hours. Thereafter, the human skin fibroblasts were divided into four groups and independently subjected to the following treatments:
(1) Control group: cells were cultivated in a MEM medium for 1 hour.
(2) "$H_2O_2$ group": cells were cultivated in a MEM medium for 1 hour, and then $H_2O_2$ was added to the medium (to the final concentration of 1 mM) to continuously treat the cells for 1 hour.
(3) "$H_2O_2$+Extract (2) group": cells were cultivated in a MEM medium that was externally added with *Pyrenaria buisanensis* extract provided by [Preparation Examples] (to the final concentration of 2 mg/mL) for 1 hour, and then $H_2O_2$ was added to the medium (to the final concentration of 1 mM) to continuously treat the cells for 1 hour.
(4) "$H_2O_2$+Extract (1) group": cells were cultivated in a MEM medium that was externally added with *Pyrenaria buisanensis* extract provided by [Preparation Examples] (to the final concentration of 1 mg/mL) for 1 hour, and then $H_2O_2$ was added to the medium (to the final concentration of 1 mM) to continuously treat the cells for 1 hour.

Thereafter, cells in each group were treated with DCFH-DA dye for 15 minutes, and then fluorescence intensity was detected by a flow cytometry at the excitation wavelength of 450 nm to 490 nm and the emission wavelength of 510 nm to 550 nm. Because ROS can convert DCFH-DA (without fluorescence) into DCF (with fluorescence), the fluorescence intensity can represent the content of ROS in cells, and the higher fluorescence intensity represents the higher content of ROS in cells. Finally, the data was analyzed by Student t-test, and the result of control group was used as a basis to calculate the content of ROS in cells of each other group. The results are shown in FIG. 1.

As shown in FIG. 1, as compared to control group, the content of ROS in "$H_2O_2$ group" significantly increased, which indicates that "$H_2O_2$ group" can imitate the situation of high content of peroxide in skin cells. However, as compared to "$H_2O_2$ group", the contents of ROS in both the "$H_2O_2$+Extract (2) group" and "$H_2O_2$+Extract (1) group" significantly decreased. These results indicate that *Pyrenaria buisanensis* extract can effectively reduce the content of ROS in skin cells, and thus, is effective in anti-oxidation.

(1-2) Examination of the Activity of SOD

Human skin fibroblasts were cultivated in a MEM medium for 24 hours. Thereafter, the human skin fibroblasts were divided into four groups and independently subjected to the following treatments:
(1) Control group: cells were cultivated in a MEM medium for 24 hours.
(2) "$H_2O_2$ group": cells were cultivated in a MEM medium for 24 hours, and then $H_2O_2$ was added to the medium (to the final concentration of 1 mM) to continuously treat the cells for 6 hours.
(3) "$H_2O_2$+Extract (2) group": cells were cultivated in a MEM medium that was externally added with *Pyrenaria buisanensis* extract provided by [Preparation Examples] (to the final concentration of 2 mg/mL) for 24 hours, and then $H_2O_2$ was added to the medium (to the final concentration of 1 mM) to continuously treat the cells for 6 hours.
(4) "$H_2O_2$+Extract (1) group": cells were cultivated in a MEM medium that was externally added with *Pyrenaria buisanensis* extract provided by [Preparation Examples] (to the final concentration of 1 mg/mL) for 24 hours, and then $H_2O_2$ was added to the medium (to the final concentration of 1 mM) to continuously treat the cells for 6 hours.

Thereafter, cells in each group were detected by using the principles of enzymatic reaction and colorimetry. Specifically, the cells in each group were subjected to the following treatment with a SOD activity assay kit (purchased from Cayman company, product number: 706002):
(a) Removing the medium and washing the cells with phosphate buffered saline (PBS), then adding trypsin (purchased from Thermo company, product number: 15400-054) to the culture plate to treat the cells for 3 minutes, and then, collecting the cells detached from the plate in a centrifuge tube and subjecting the same to a centrifugation at 400 g for 5 minutes; then, removing the supernatant from the tube, washing the cells with PBS, and subjecting the tube to a centrifugation at 400 g for 5 minutes, and then, removing the supernatant from the tube again;

(b) Adding 50 μL of cell extraction solution to the tube and subjecting the tube to a centrifugation at 12000 g, 4° C. for 30 minutes, and then, removing the insoluble to provide a cell liquid extract;

(c) Mixing 10 μL of cell liquid extract obtained from step (b) with 200 μL of tetrazolium salt solution as well as 20 μL of xanthine oxidase solution evenly to react for 30 minutes;

(d) Measuring the absorbance of the product of step (c) by using an enzyme-linked immunosorbent assay (ELISA) reader (purchased from Epoch company, product number: 1212171) at the wavelength of 450 nm; and (e) Replacing the cell liquid extract used in step (c) with a SOD standard, repeating the operations from steps (c) to (d), and recording the absorbance of the product thus obtained (hereinafter referred to as "SOD standard absorbance").

Thereafter, the SOD standard absorbance obtained from step (e) was used as a basis to calculate the activity of SOD of cells in each group according to the formula provided by the instruction manual of the SOD activity assay kit (purchased from Cayman company, product number: 706002). The results are shown in FIG. 2.

Figure 2:
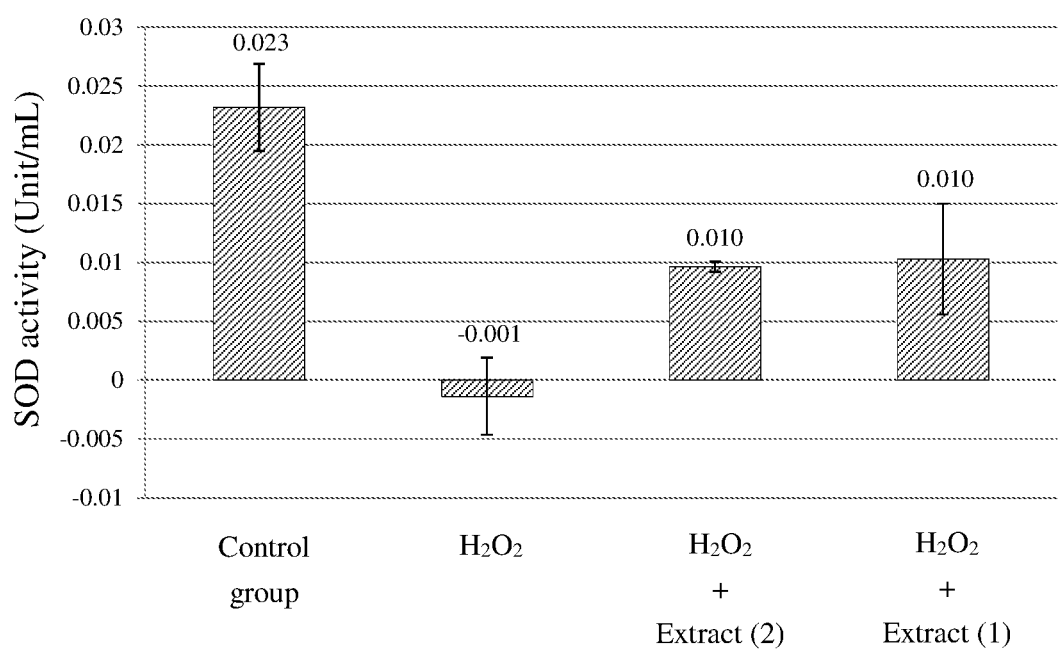
FIG. 2 shows the effect of the *Pyrenaria buisanensis* extract of the present invention on enhancing the activity of SOD in cells, wherein the cells in the control group were cultivated in a medium free of *Pyrenaria buisanensis* extract for 24 hours, those in the "$H_2O_2$ group" were cultivated in a medium free of *Pyrenaria buisanensis* extract for 24 hours, and then treated with $H_2O_2$ for 6 hours, and those in the "$H_2O_2$+extract (1) group" and "$H_2O_2$+extract (2) group" were independently cultivated in a medium that was externally added with *Pyrenaria buisanensis* extract (to the final concentration of 1 mg/mL and 2 mg/mL, respectively) for 24 hours and then treated with $H_2O_2$ for 6 hours.

As shown in FIG. 2, the activity of SOD of cells in "$H_2O_2$ group" was extremely low. However, under an oxidative stress induced by $H_2O_2$, the activities of SOD of cells in the groups treated with *Pyrenaria buisanensis* extract (including "$H_2O_2$+Extract (2) group" and "$H_2O_2$+Extract (1) group") significantly increased. These results indicate that *Pyrenaria buisanensis* extract can effectively enhance the activity of SOD in skin cells, and thus, is beneficial to the decomposition of peroxide and is effective in anti-oxidation.

Example 2

Effects of *Pyrenaria buisanensis* Extract on Increasing the Expressions of SOD2, CAT and MSH2 Genes Human skin fibroblasts were cultivated in a MEM medium for 24 hours. Thereafter, the human skin fibroblasts were divided into six groups and independently subjected to the following treatments:
(1) Control group: cells were cultivated in a MEM medium for 6 hours.
(2) "UVA group": cells were cultivated in a MEM medium for 6 hours, and then irradiated with UVA (15 J/cm$^2$) for 6 hours.
(3) "Extract (1)—6 hr group" and "Extract (1)—24 hr group": cells were independently cultivated in a MEM medium that was externally added with *Pyrenaria buisanensis* extract (to the final concentration of 1 mg/mL) for 6 hours and 24 hours respectively, and then irradiated with UVA (15 J/cm$^2$) for 6 hours.
(4) "Extract (2)—6 hr group" and "Extract (2)—24 hr group": cells were independently cultivated in a MEM medium that was externally added with *Pyrenaria buisanensis* extract (to the final concentration of 2 mg/mL) for 6 hours and 24 hours respectively, and then irradiated with UVA (15 J/cm$^2$) for 6 hours.

Thereafter, cells in each group were harvested and subjected to an RNA extraction with an RNA extraction kit (purchased from Geneaid company). Then, the RNA thus provided was transcribed into cDNA with a reverse transcriptase (SuperScript® III Reverse Transcriptase; purchased from Invitrogen company). The cDNA thus provided was subjected to a quantitative polymerase chain reaction (qPCR) by using an ABI Step One Plus system and a KAPA SYBR FAST qPCR kit to determine the expression levels of SOD2, CAT and MSH2 genes. Finally, the data was analyzed by Student t-test, and the result of control group was used as a basis (i.e., the gene expression level of control group was set as 1-fold) to calculate the relative gene expression levels of the other groups. The results are shown in FIGS. 3 to 5.

Figure 3:
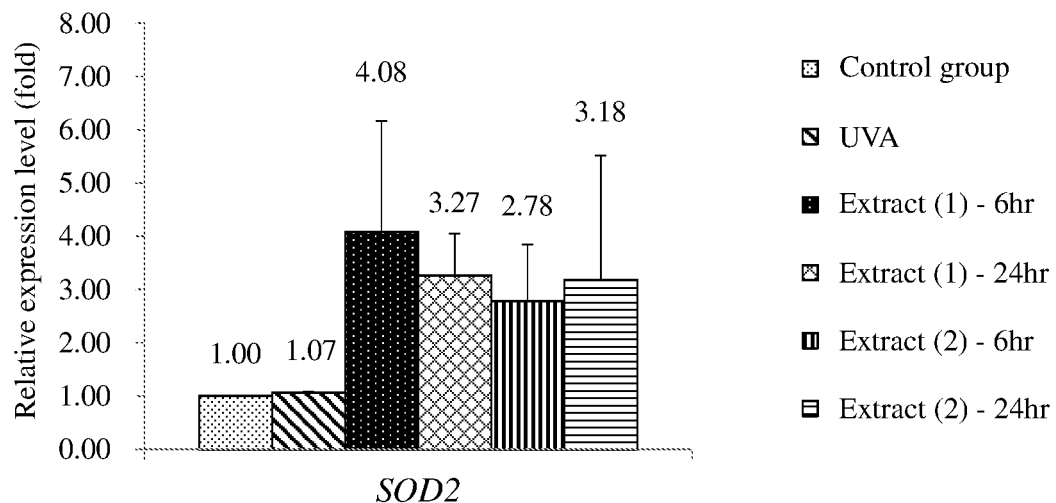
Figure 4:
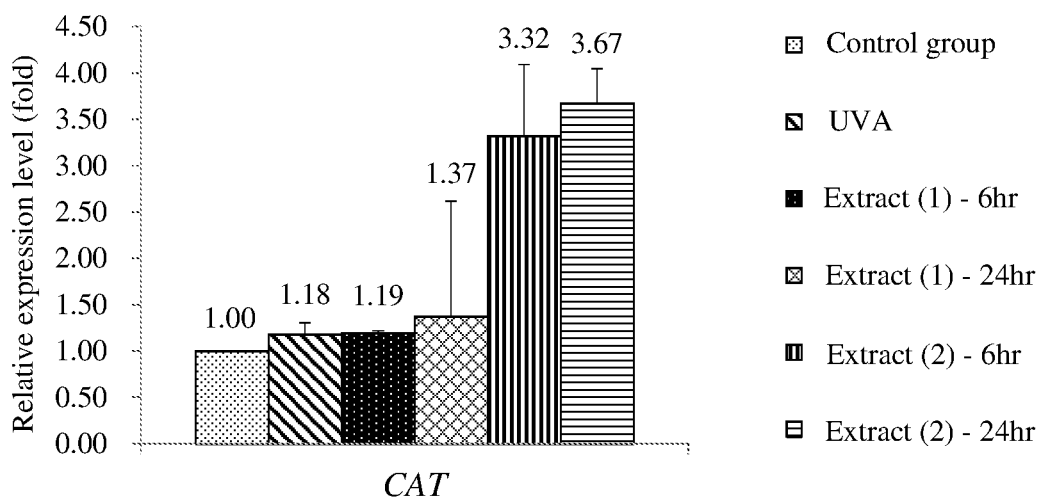
Figure 5:
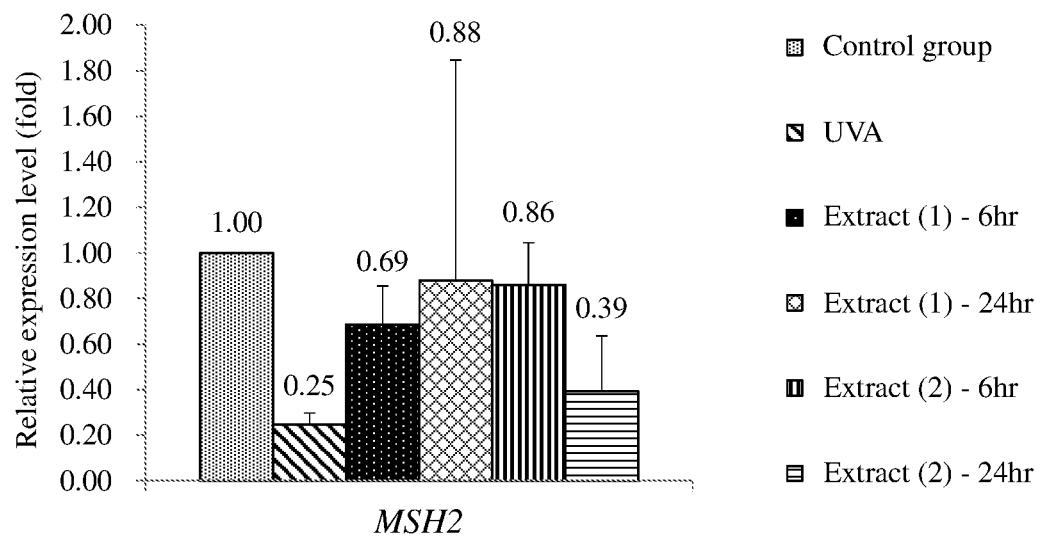

As shown in FIGS. 3 to 5, as compared to "UVA group", the expression levels of SOD2 and MSH2 genes of cells in "Extract (1)—6 hr group", "Extract (1)—24 hr group", "Extract (2)—6 hr group", and "Extract (2)—24 hr group" all significantly increased. The expression level of CAT gene of cells in "Extract (2)—6 hr group" and "Extract (2)—24 hr group" also significantly increased. These results indicate that *Pyrenaria buisanensis* extract can increase the expression levels of SOD2, CAT and MSH2 genes effectively, and thus, can be used for enhancing the antioxidant capability of cells, assisting in repairing damaged DNA and proteins, thereby providing the effects of anti-skin aging, anti-photodamage and repairing skin tissues, and also can be used for preventing cardiovascular disease, treating cardiovascular disease, preventing diabetes, treating diabetes, preventing Alzheimer's disease, and/or treating Alzheimer's disease.

Example 3

Effects of *Pyrenaria buisanensis* Extract on Increasing the Expressions of FLG, HAS3, GBA, Tgm1 and Keratin14 Genes Human primary epidermal keratinocytes (HPEK-50; purchased from CELLnTEC company, product number: PR3D-HPEK-50) were cultivated in a Keratinocyte-SFM medium (purchased from Thermo company, product number: 17005042) for 24 hours. Thereafter, the human primary epidermal keratinocytes were divided into two groups and independently subjected to the following treatments:
(1) Control group: cells were cultivated in a Keratinocyte-SFM medium for 6 hours.
(2) "Extract group": cells were cultivated in a Keratinocyte-SFM medium that was externally added with *Pyrenaria buisanensis* extract provided by [Preparation Examples] (to the final concentration of 0.03125 mg/mL) for 6 hours.

Thereafter, cells in each group were harvested and subjected to an RNA extraction with an RNA extraction kit (purchased from Geneaid company). Then, the RNA thus provided was transcribed into cDNA with a reverse transcriptase (SuperScript® III Reverse Transcriptase; purchased from Invitrogen company). The cDNA thus provided was subjected to a quantitative polymerase chain reaction (qPCR) by using an ABI Step One Plus system and a KAPA SYBR FAST qPCR kit to determine the expression levels of FLG, HAS3, GBA, Tgm1 and Keratin14 genes. Finally, the data was analyzed by SCORE method, and the result of control group was used as a basis (i.e., the gene expression level of control group was set as 1-fold) to calculate the relative gene expression levels of the other groups. The results are shown in FIGS. 6 to 8.

Figure 6:
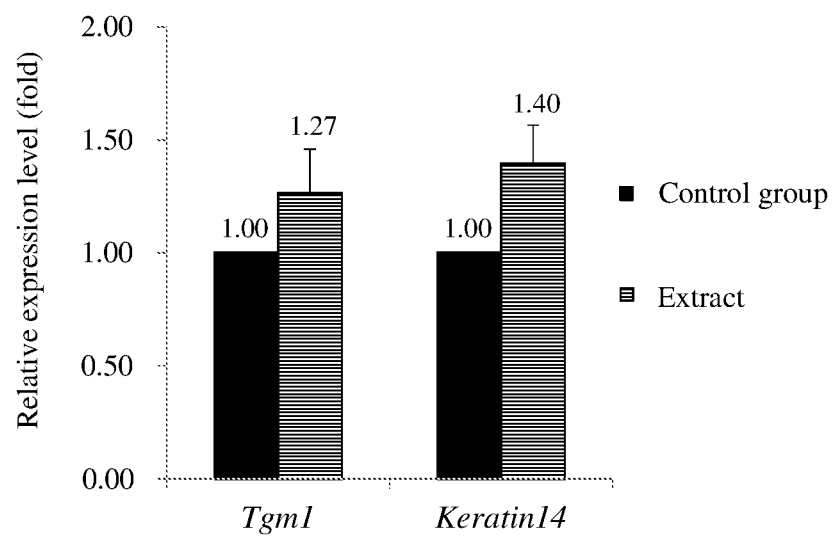
Figure 7:
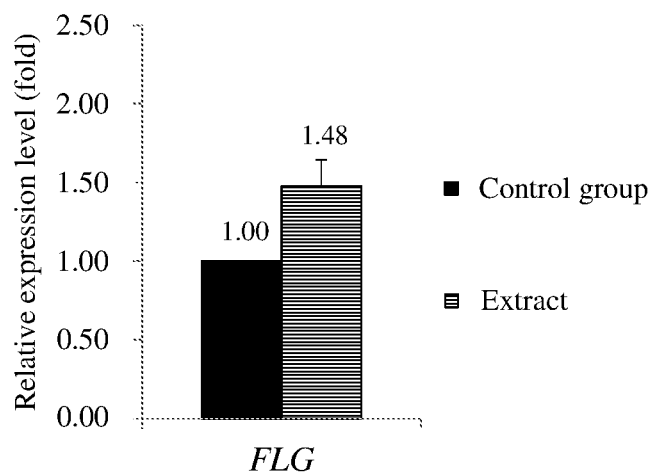
Figure 8:
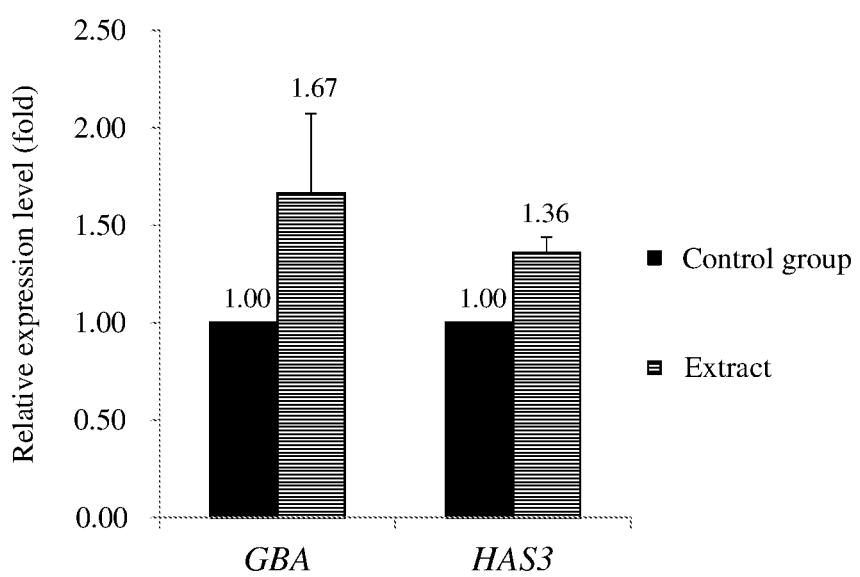

As shown in FIGS. 6 to 8, as compared to control group, the expression levels of Tgm1, Keratin14, FLG, GBA and HAS3 genes of cells in "Extract group" all significantly increased. These results indicate that *Pyrenaria buisanensis* extract can increase the expression levels of Tgm1, Keratin14, FLG, GBA and HAS3 genes effectively, and thus, can be used for maintaining cell structure, assisting in the formation of skin barrier, increasing the synthesis of hyaluronic acid, and increasing the water content of cells, thereby achieving the effects of moisturizing skin, tightening skin, reducing skin fine lines, and/or alleviating dry skin, and also can be used for anti-skin aging, preventing a disease related to dry skin and/or treating a disease related to dry skin.

Example 4

Human Clinical Trial

The experimentation was carried out in a self-control way. At week 0 (i.e., prior to staring applying the *Pyrenaria buisanensis* essence, which contains 1% *Pyrenaria buisanensis* extract provided by [Preparation Examples], based on the total weight of the essence), 10 volunteers detected and recorded the water content of their facial skin by using a DermaLab® Combo skin analyzer and a water content measuring probe, detected and recorded the melanin of their facial skin by using a C+K electronic Mexameter® MX18 analyzer and an erythema measuring probe, and detected and recorded the skin sagging level by using a C+K electronic MPA580 skin elasticity analyzer. Thereafter, each volunteer applied the *Pyrenaria buisanensis* essence (containing 1% *Pyrenaria buisanensis* extract provided by [Preparation Examples], based on the total weight of the essence) over half side of their face and applied the essence containing placebo alone (i.e., free of *Pyrenaria buisanensis* extract of the present invention, but other ingredients all were same as the essence) to the other half side of their face every morning and evening for 6 weeks, and then, measured and recorded the melanin of skin, skin sagging and water content of skin of each half side of face by a multifunctional skin analyzer. Then, the data thus obtained was analyzed by Student t-test, and the result of week 0 was used as a basis (i.e., the result of week 0 was set as 100%) to calculate the melanin of skin, skin sagging and water content of skin after applying the essences for 6 weeks. The results are shown in FIGS. 9 to 11.

Figure 9:
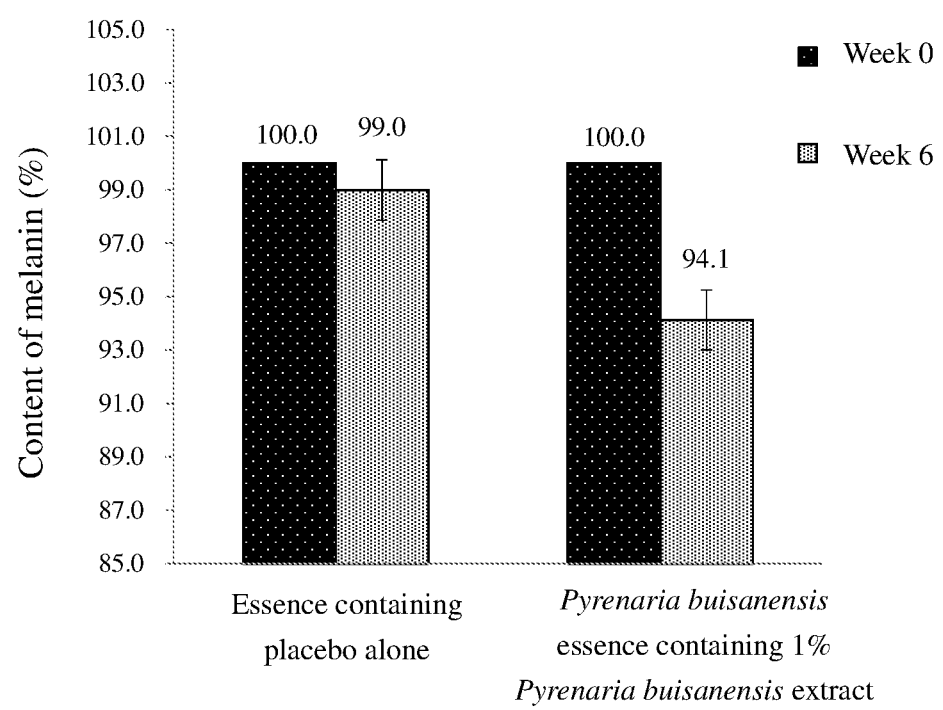
FIG. 9, FIG. 10 and FIG. 11 respectively show the effects of the *Pyrenaria buisanensis* extract of the present invention on reducing melanin of skin, reducing skin sagging, and increasing the water content of skin.
Figure 10:
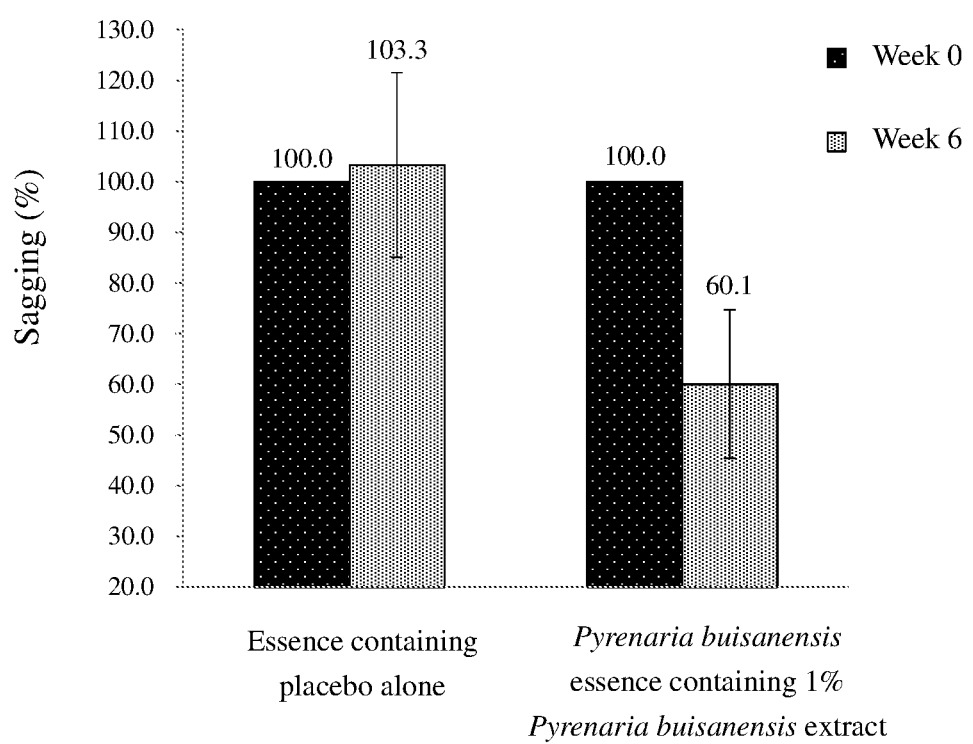
Figure 11:
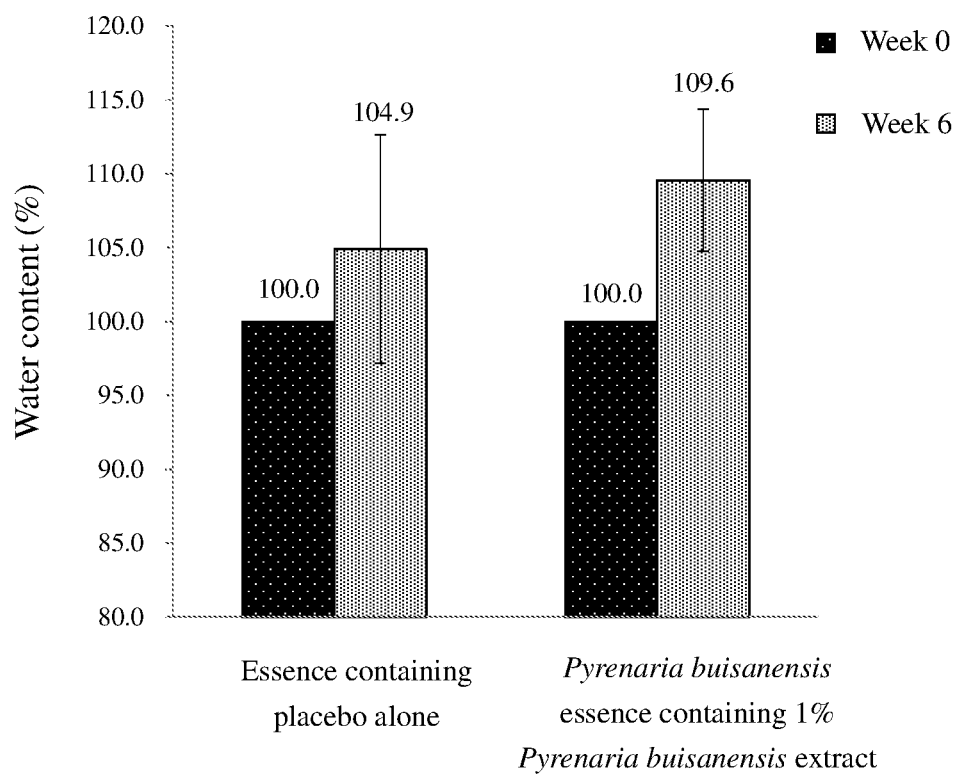

As shown in FIGS. 9 to 11, after applying the *Pyrenaria buisanensis* essence containing *Pyrenaria buisanensis* extract of the present invention on the skin for 6 weeks, the melanin of skin and skin sagging of the subjects significantly reduced, and the water content of skin significantly increased. These results indicate that *Pyrenaria buisanensis* extract of the present invention is effective in moisturizing skin, whitening skin, tightening skin, and reducing skin fine lines.

What is claimed is:

1. A method for at least one of whitening skin, improving skin condition, anti-skin aging, assisting in maintenance of skin health, anti-photodamage, repairing skin tissues, preventing a disease related to dry skin and treating skin disease, comprising administering to a subject in need an effective amount of a *Pyrenaria buisanensis* extract.

2. The method as claimed in claim 1, wherein the extract is provided by extracting *Pyrenaria buisanensis* with a polar solvent, and the polar solvent is selected from a group consisting of water, C1-C4 alcohols, and combinations thereof.

3. The method as claimed in claim 1, wherein the extract is an extract of leaves of *Pyrenaria buisanensis*.

4. The method as claimed in claim 3, wherein the extract is provided by extracting the leaves of *Pyrenaria buisanensis* with a polar solvent, and the polar solvent is selected from a group consisting of water, C1-C4 alcohols, and combinations thereof.

5. The method as claimed in claim 1, which is for moisturizing skin, tightening skin, reducing skin fine lines, and/or alleviating dry skin.

6. The method as claimed in claim 5, wherein the extract is administered to the subject by at least one of transdermal administration, oral administration, and subcutaneous injection.

7. The method as claimed in claim 1, wherein the extract is administered to the subject by at least one of transdermal administration, oral administration, and subcutaneous injection.

8. The method as claimed in claim 1, which is for at least one of whitening skin, improving skin condition, anti-skin aging, assisting in maintenance of skin health, anti-photodamage, repairing skin tissues, preventing a disease related to dry skin and treating skin disease by increasing the expressions of SOD2 gene, CAT gene, MSH2 gene, Tgm1 gene, Keratin14 gene, FLG gene, GBA gene, and/or HAS3 gene.

9. A method for at least one of treating cardiovascular disease, treating diabetes, and treating neurodegenerative disease, comprising administering to a subject in need thereof a therapeutically effective amount of a *Pyrenaria buisanensis* extract sufficient to increase the expression of one or more gene selected from the group consisting of SOD2, CAT, MSH2, Tgm1, Keratin14, FLG, GBA, and HAS3.

10. The method as claimed in claim 9, wherein the extract is provided by extracting *Pyrenaria buisanensis* with a polar solvent, and the polar solvent is selected from a group consisting of water, C1-C4 alcohols, and combinations thereof.

11. The method as claimed in claim 9, wherein the extract is an extract of leaves of *Pyrenaria buisanensis*.

12. The method as claimed in claim 11, wherein the extract is provided by extracting the leaves of *Pyrenaria buisanensis* with a polar solvent, and the polar solvent is selected from a group consisting of water, C1-C4 alcohols, and combinations thereof.

13. The method as claimed in claim 9, wherein the cardiovascular disease is stroke, and the neurodegenerative disease is Alzheimer's disease.

14. The method as claimed in claim 13, wherein the extract is administered to the subject by at least one of transdermal administration, oral administration, and subcutaneous injection.

15. The method as claimed in claim 9, wherein the extract is administered to the subject by at least one of transdermal administration, oral administration, and subcutaneous injection.

* * * * *